United States Patent
Zou et al.

(10) Patent No.: US 9,944,574 B2
(45) Date of Patent: Apr. 17, 2018

(54) CONTINUOUS PREPARATION METHOD OF HIGH-PURITY QUADRICYCLANE

(71) Applicant: TIANJIN UNIVERSITY, Tianjin (CN)

(72) Inventors: Jijun Zou, Tianjin (CN); Xiangwen Zhang, Tianjin (CN); Li Wang, Tianjin (CN); Qingfa Wang, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 14/409,448

(22) PCT Filed: May 23, 2014

(86) PCT No.: PCT/CN2014/078212
§ 371 (c)(1),
(2) Date: Dec. 18, 2014

(87) PCT Pub. No.: WO2015/120670
PCT Pub. Date: Aug. 20, 2015

(65) Prior Publication Data
US 2016/0340273 A1 Nov. 24, 2016

(30) Foreign Application Priority Data

Feb. 17, 2014 (CN) .......................... 2014 1 0052297

(51) Int. Cl.
*B01J 19/12* (2006.01)
*B01J 35/00* (2006.01)
(Continued)

(52) U.S. Cl.
CPC .......... *C07C 5/2266* (2013.01); *B01J 19/123* (2013.01); *B01J 31/0208* (2013.01);
(Continued)

(58) Field of Classification Search
CPC .............. C07C 5/2266; C07C 2103/90; C07C 2531/38; C07C 2531/34; C07C 2531/36;
(Continued)

(56) References Cited

U.S. PATENT DOCUMENTS 3,350,291 A * 10/1967 Srinivasan ........... B01J 31/2295
204/158.14
4,012,305 A * 3/1977 Fischer .................... C07C 2/42
204/157.99
(Continued)

FOREIGN PATENT DOCUMENTS

CN 103787819 A 5/2014

*Primary Examiner* — Ibrahime A Abraham
*Assistant Examiner* — Colleen M Raphael
(74) *Attorney, Agent, or Firm* — Morgan, Lewis & Bockius LLP; Jeffry S. Mann (57) ABSTRACT

The invention discloses a continuous process for producing high-pure quadricyclane, in which "a reaction-rectification integral process" or "a reaction followed by rectification process" may be employed. The two processes both use a novel composite catalyst which is obtained by loading an organic photo-sensitizer on a solid photocatalyst, and the composite catalyst has a high activity and a good stability. In the reaction-rectification integral process, the composite catalyst is used by being blended with rectification fillers or covering the rectification fillers, so as to achieve the integration of the reaction and the rectification. In the reaction followed by rectification process, the composite catalyst and the rectification fillers are placed separately from each other. The two processes achieve a relatively short residence time of reactants, produce highly-pure quadricyclane, and reduce the formation of cokes.

8 Claims, 5 Drawing Sheets

(51) Int. Cl.
    *C07C 5/22*     (2006.01)
    *B01J 31/02*     (2006.01)
    *B01J 31/34*     (2006.01)
    *B01J 31/36*     (2006.01)
    *B01J 31/38*     (2006.01)
    *B01J 31/26*     (2006.01)

(52) U.S. Cl.
CPC ....... *B01J 31/0237* (2013.01); *B01J 31/0239* (2013.01); *B01J 31/0271* (2013.01); *B01J 35/004* (2013.01); *C07C 5/222* (2013.01); *C07C 5/2213* (2013.01); *B01J 31/26* (2013.01); *B01J 31/34* (2013.01); *B01J 31/36* (2013.01); *B01J 31/38* (2013.01); *C07C 2521/06* (2013.01); *C07C 2523/02* (2013.01); *C07C 2523/06* (2013.01); *C07C 2523/20* (2013.01); *C07C 2523/30* (2013.01); *C07C 2531/02* (2013.01); *C07C 2531/26* (2013.01); *C07C 2531/34* (2013.01); *C07C 2531/36* (2013.01); *C07C 2531/38* (2013.01); *C07C 2603/86* (2017.05); *Y02P 20/582* (2015.11)

(58) Field of Classification Search
CPC ... C07C 2531/26; C07C 5/2213; C07C 5/222; C07C 2603/86; C07C 2531/02; C07C 2523/02; C07C 2521/06; C07C 2523/30; C07C 2523/20; C07C 2523/06; B01J 31/0237; B01J 31/0271; B01J 35/004; B01J 31/0208; B01J 31/26; B01J 31/38; B01J 31/36; B01J 31/34; B01J 31/0239
USPC .................................................. 204/158.14
See application file for complete search history.

(56) References Cited

U.S. PATENT DOCUMENTS

| | | | | |
|---|---|---|---|---|
| 4,394,858 | A * | 7/1983 | Giordano | C09K 5/16 204/158.14 |
| 4,725,342 | A * | 2/1988 | Crabtree | C07C 2/76 204/158.14 |
| 5,545,790 | A * | 8/1996 | Wu | C07C 2/42 585/20 |
| 2004/0214103 | A1 * | 10/2004 | Araki | C07C 33/44 430/270.1 |
| 2016/0340273 | A1 | 11/2016 | Zou et al. | |

* cited by examiner

CONTINUOUS PREPARATION METHOD OF HIGH-PURITY QUADRICYCLANE

CROSS-REFERENCE TO RELATED APPLICATIONS

This application is a 371 of PCT/CN2014/078212 filed May 23, 2014 which claims benefit of CN 201410052297.6 filed on Feb. 17, 2014, both of which are incorporated herein by reference in their entireties.

FIELD OF THE INVENTION

The invention is in the field of the quadricyclane synthesis.

BACKGROUND OF THE INVENTION

The quadricyclane, being an important high-energy aerospace fuel, has a density of up to 0.98 g.cm$^{-3}$, and the ice point lower than –40° C., and can be used in propelling systems of aerospace vehicles, for example, such as rockets, guided missiles, satellites, and space crafts. As compared with kerosene fuels, the quadricyclane has the high-energy advantage, and as compared with hydrazine fuels, it has the advantage of the high safety.

The quadricyclane may be synthesized via a photochemical process, that is, norbornadiene, as the starting material, is used to form the quadricyclane via the intermolecular addition reaction of norbornadiene with ultraviolet radiations and in the presence of an organic photo-sensitizer or a solid photocatalyst as the catalyst for the reaction.

Current photo-catalytic isomerisation reaction of norbornadiene is conducted by utilizing high-voltage or medium-voltage mercury arc lamps, and however, because light radiations will produce large quantities of heat energies, a quartz cooling jacket which is transparent to ultraviolet lights is necessary so as to cool the reaction system. During the light induced isomerisation, some side reactions will be involved, and the main of them is that the reactants are polymerized under light induction to form some cokes which adhere on the outer surface of the quartz jacket so that the light transmission is hindered, thereby resulting in that the reaction become slow even is stopped. In addition, the quartz reactor is hardly to clean and is fragile and high cost.

In the U.S.A patent US2004/0054244A1, in order to inhibit coking side reactions during the reaction, amine inhibitors are added to the reactants, and a flowing circulation quarters reactor is designed. In the reactor, a 1300 W medium-voltage mercury arc lamp is employed; the reaction solution containing 0.4 wt % ethyl Michier's Ketone is allowed to flow through the reactor with the rate of 1.2 ml/min; and after the reaction is circulated for 25 hours, the conversion rate is close to 100%. In the process of the patent, the photo-sensitizer is directly left in the resultant quadricyclane without any purification.

In the German patent DE3625006A1, a rotary brush is designed. The reaction is conducted by utilizing photo-sensitizers, and during the reaction, the brush is periodically used to clean cokes on the wall of the quartz reactor.

Although the processes as described in the above patents inhibit coking in some extent, the following disadvantages are still involved: (1) reactors are made of quartz which is in high cost and fragile; (2) photo-sensitizers are remained in the product, and it can influence the purity of quadricyclane; (3) in views of the reaction mechanisms, it is impossible to completely inhibit the coking reaction, and thus after a long time reaction, there are always some cokes formed on the wall of the reactor; and (4) the reactions are in the intermittent manner which is disadvantageous to large-scale productions.

In order to overcome the above difficulties, the objective of the invention is to provide a novel process for producing quadricyclane wherein a continuous process for producing highly-pure quadricyclane can be achieved by integrating the reaction and the purification.

BRIEF DESCRIPTION OF THE DRAWINGS

Individual reference sign in the above figures has the following meanings: 1. norbornadiene; 2. reaction-rectification integral reactor; 3. distiller; 4 highly pure quadricyclane; 5. stainless steel cylinder; 6. composite catalyst-filler layer; 7. quartz tube; 8. ultraviolet light source; 9. norbornadiene storage tank; 10. reactor; 11. rectification column; 12. cokes.

SUMMARY OF THE INVENTION

The first aspect of the invention relates to a continuous process for producing highly-pure quadricyclane, which is a reaction-rectification integral process, comprising the following steps: (a) a norbornadiene reactant is introduced into a reaction-rectification integral reactor; the reactor comprises a stainless steel cylinder in the outside, and a quartz tube is arranged inside of the reactor; an ultraviolet light source is arranged in the quartz tube, and rectification fillers and a composite catalyst are filled between the quartz tube and the stainless steel cylinder, wherein the rectification fillers are disorderly mixed with the composite catalyst in the particulate form, or the surface of the rectification fillers is covered with a layer of the composite catalyst; the introduced norbornadiene in a form of a liquid film or a gas-liquid mixture flows through the surface and inner channels of the composite catalyst so that a reaction is conducted to produce a reaction product comprising quadricyclane and cokes and simultaneously, (b) under the rectification action provided by the reaction-rectification integral reactor, the norbornadiene gradually moves toward the top of the reaction-rectification integral reactor and the reaction continues; unreacted norbornadiene leaves from the top and after being condensed, it returns the reaction-rectification integral reactor as the circulating reactant; the product quadricyclane and cokes can move toward the bottom of the reaction-rectification integral reactor under the action of rectification and are discharged from the bottom to a distiller in which the distillation is conducted; at last, the quadricyclane in the purity of more than 99.5% is produced on the top of the distiller, and the cokes are remained in the bottom of the distiller.

The second aspect of the present invention relates to a process for producing highly-pure quadricyclane, which is a reaction followed by rectification process, comprising the following steps: a. a norbornadiene reactant is introduced into a reactor; the reactor comprises a stainless steel cylinder in the outside, and a quartz tube is arranged inside of the reactor; an ultraviolet light source is arranged in the quartz tube, and a composite catalyst is filled between the quartz tube and the stainless steel cylinder; the introduced norbornadiene flows through the surface and inner channels of the composite catalyst in a form of a liquid film so that a reaction is conducted to produce a reaction product comprising quadricyclane and cokes; and then (b) all the materials are fed into a rectification column, and under the rectification action, unreacted norbornadiene, as the tops, leaves from the top of the rectification column and returns to the aforesaid reactor as the circulating reactant; the quadricyclane and cokes, as the bottoms, leave the rectification column; and then (c) the aforesaid bottoms are fed into a distiller to conduct distillation; the quadricyclane in the purity of more than 99.5% is produced on the top of the distiller, and cokes are remained in the bottom of the distiller.

In the first and second aspects of the invention, the composite catalyst comprises a solid photocatalyst which is selected from $TiO_2$, Ti-MCM-41, Ti-SBA-15, ZnO, $WO_3$, $Ta_2O_5$ or $SrTiO_3$, and an organic photo-sensitizer loaded on the surface or channels of the solid photocatalyst which is selected from benzophenone, acetophenone, Michler's Ketone, tetraethyl Michler's Ketone, and diethyl Michler's Ketone, wherein the organic photo-sensitizer is present in an amount of 0.5 to 20% by weight of the solid photocatalyst.

In the first and second aspects, the ultraviolet light source is used to provide ultraviolet light, to initiate the light induced isomerisation reaction. The quartz tube per se is chemically inert, and has certain toughness so that it can protect the ultraviolet light source. Furthermore, because the quartz tube is transparent, it can allow the ultraviolet light to transmit through it.

In the first or second aspect of the invention, said reaction-rectification integral reaction or said reactor can be designed into a detachable structure according to actual needs, to facilitate clean or replace the catalyst and the rectification fillers or to clean or replace the catalyst, and check or maintain the quartz tube and the ultraviolet light source.

The structural parameters of the reaction-rectification integral reactor in the first aspect are as follows: the radial thickness of the rectification fillers and composite catalyst filled between the quartz tube and the stainless steel cylinder ranges from 1 to 10 cm, and the height of the reactor is not less than 100 cm. Certainly, the concrete parameters may be adjusted according to the amount of the materials to be treated.

The process conditions of the reaction-rectification integral reactor in the first aspect are as follows: the temperature on the top of the reactor ranges from 90 to 95° C.; the temperature on the bottom of the reactor ranges from 100 to 105° C.; the pressure is an atmospheric pressure; and the reflux ratio ranges from 0.5 to 2.

The process conditions of the distiller in the first aspect are as follows: the temperature is from 60 to 65° C., and the pressure is from 90 to 110 mBar. All the pressures here are Gage pressures.

The process conditions of the reactor in the second aspect are as follows: the radial thickness of the composite catalyst ranges from 1 to 10 cm; there are no specific requirements to the temperature; and the pressure is an atmospheric pressure.

The process conditions of the rectification column in the second aspect are as follows: the height of the column is not lower than 100 cm; the temperature on the top of the column is from 90 to 95° C.; the temperature on the bottom of the column is from 100 to 105° C.; the pressure is an atmospheric pressure, and the reflux ratio ranges from 0.5 to 2.

The process conditions of the distiller in the second aspect are as follows: the temperature ranges from 60 to 65° C., and the pressure is from 90 to 110 mBar.

The catalyst used in the invention is a composite catalyst, i.e., the combination of an organic photo-sensitizer and a solid photocatalyst. The inventor surprisingly finds out that after the organic photo-sensitizer is loaded on the solid photocatalyst, the two substances can produce certain synergetic effects which can significantly increase the efficiency of light induced isomerisation reaction, that is, when the reaction is conducted in a intermittent stirring manner, the reaction time can be reduced from 20 hours in the prior art to be 10 hours or less. Furthermore, the invention further uses a fixed bed reactor structure. The fixed bed reactor can allow reactants, in the form of a liquid membrane or a gas-liquid mixture, flow through the surface and inner channels of the composite catalyst, so that the reactants can have a larger contact area with the catalyst, thereby resulting in a higher light efficiency. Furthermore, the reactor can accelerate the reaction by utilizing a higher temperature than that in a stirring reaction. Since it is unnecessary to take the cooling of the light source into account, a light source having a higher power can be used so that on the proviso that the product yield is specified, the reaction can reduce the reaction time as compared with customary stirring reactions. Hence, in the invention, the single-pass residence time of the reactants can be reduced to be 40 to 130 minutes. The reduction of the single-pass residence time can greatly reduce the coking side reactions, which will be advantageous to reduce the formation of cokes and to maintain the reactor clean, thereby to benefit the long time and stable operations of the reactor.

An important characteristic of the first aspect of the invention is to utilize a reaction-rectification integral reactor. Rectification fillers and a composite catalyst are filled between the quartz tube and the stainless steel cylinder, wherein the rectification fillers and the composite catalyst are mixed together disorderly, or alternatively, the surface of the rectification fillers is covered with a layer of the composite catalyst, and thus the reactor can also play a role of a rectification column. During the reaction, the norbornadiene having a lower boiling point moves toward the top of the reactor and continuously reacts during the moving procedure, and quadricyclane and cokes having a higher boiling points move toward the bottom of the reactor. The process either can achieve the isomerisation of norbornadiene into quadricyclane, or can achieve the online and instant separation of the norbornadiene from the reaction product quadricyclane and cokes, and thus the cokes can be separated from the reaction system once they are produced, which can further assure the continuity and stability of the process procedure. The rectification fillers are selected from conventional rectification fillers, for example, corrugated fillers, rasching ring fillers, θ-shaped fillers and special shaped fillers. These rectification fillers generally have the characteristic of a large surface area, and they are often in the frame hollow structure. The rectification fillers can be mixed with the above composite catalyst particles in a very high spatial compactedness, or alternatively, the above composite catalyst can be directly applied on the surface of the rectification fillers via conventional catalyst moulding techniques or fixing technical, and then the rectification fillers and the composite catalyst are filled into the reaction-rectification integral reactor for the use.

The characteristic of the second aspect of the invention relates to the conventional reaction followed by rectification process, in which the composite catalyst particles are arranged in the reactor, and the rectification fillers are arranged in the rectification column, they being not in the same one container. The specific illustrations to the composite catalyst and the rectification fillers are the same as those in the first aspect.

EXAMPLES

Figure 1:
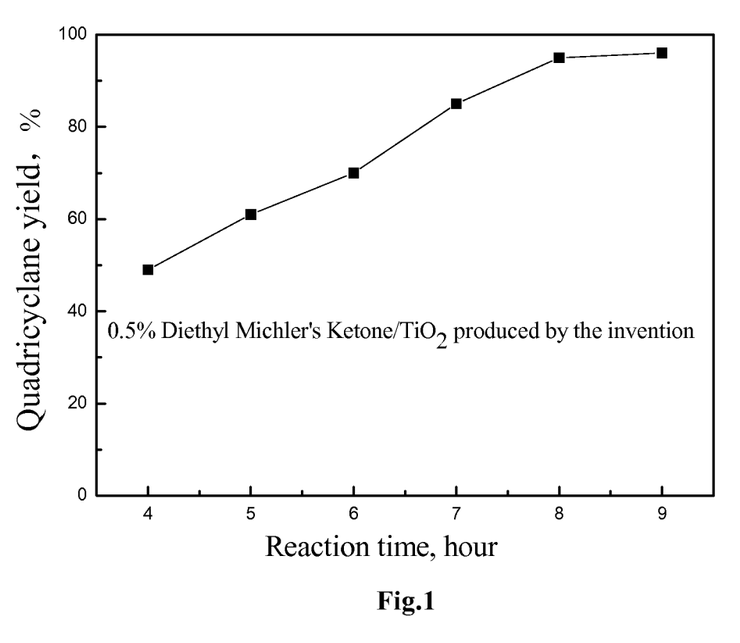
FIG. 1 shows the variation of the quadricyclane yield in the presence of a catalyst according to the invention with time.

The invention is further described via the following examples. The examples are only illustrative, but not limiting.

of 10-70° C., the resulting mixture is irradiated for 8 hours with a 400 W high-voltage mercury lamp to effect the reaction; the solution composition is analyzed periodically with the chromatograph analysis, and the yield of the target product quadricyclane is calculated. The yields in different reaction time are shown in FIG. 1, and the quadricyclane yields corresponding to individual catalysts are show in Table 1 also.

In addition, under the same experimental conditions, the activity of a single organic photo-sensitizer, the activity of a single solid photocatalyst, and the activity of a simple physical mixture of the organic photo-sensitizer and the solid photocatalyst are measured, and these catalysts which are not prepared by the process of the invention are embodied in comparative examples.

TABLE 1

|   | Catalysts | The weight ratio of catalyst to norbornadiene | Reaction temperature | Quadricyclane yield |
|---|---|---|---|---|
| Example 1 | 0.5% diethyl Michler's Ketone/TiO$_2$ | 10% | 50° C. | 95.1% |
| Comparative Example 1 | diethyl Michler's Ketone | 10% | 50° C. | 23% |
| Comparative Example 2 | TiO$_2$ | 10% | 50° C. | 16% |
| Comparative Example 3 | A physical mixture of 0.5% diethyl Michler's Ketone and TiO$_2$ | 10% | 50° C. | 34% |
| Example 2 | 2% diethyl Michler's Ketone/Ti-MCM-41 | 8% | 10° C. | 94.3% |
| Example 3 | 5% diethyl Michler's Ketone/Ti-SBA-15 | 2% | 20° C. | 93.0% |
| Example 4 | 9% ethyl Michler's Ketone/ZnO | 4% | 30° C. | 95.4% |
| Example 5 | 12% diethyl Michler's Ketone/WO$_3$ | 7% | 40° C. | 96.0% |
| Example 6 | 15% diethyl Michler's Ketone/Ta$_2$O$_3$ | 5% | 60° C. | 92.2% |
| Example 7 | 20% diethyl Michler's Ketone/SrTiO$_3$ | 2% | 70° C. | 94.5% |
| Example 8 | 15% acetophenone/TiO$_2$ | 8% | 70° C. | 95.3% |
| Example 9 | 10% benzophenone/WO$_3$ | 5% | 40° C. | 93.7% |
| Example 10 | 5% Michler's Ketone/Ta$_2$O$_5$ | 7% | 50° C. | 90.2% |
| Example 11 | 2% tetraethyl Michler's Ketone/SrTiO$_3$ | 2% | 60° C. | 92.5% |

1. Preparation of the Composite Catalyst

Selections and combinations of specific organic photo-sensitizers and solid photocatalysts are shown in Table 1. Concrete preparations for a composite catalyst are as follows: an organic photo-sensitizer is dissolved in an organic solvent (e.g., ethanol) to formulate a solution with the weight concentration of 20 wt %, and a solid photocatalyst is dried at 100° C.; the organic photo-sensitizer containing solution and the dried solid photocatalyst are mixed in the weight ratio of organic photo-sensitizer to solid photocatalyst of 0.5 to 20 wt %, and the mixture is stirred for 24 hours so that the organic photo-sensitizer can be sufficiently adsorbed onto the solid photocatalyst; thereafter, the redundant solution is filtered and the solid is dried at vacuum at 100° C. for 5 hours (there are no special requirements to the vacuum degree), to give the composite catalyst of the invention. The catalyst prepared by the process of the invention is embodied in the examples.

2. Tests for the Catalytic Activity of the Catalyst

The above catalyst particles are added to 150 ml of norbornadiene with the weight ratio of catalyst particles to norbornadiene of 2 to 10 wt %, and under the conditions of nitrogen protection and magnetic stirring and a temperature 3. Analyses to Experimental Results of Catalytic Activity As shown in FIG. 1, when the composite catalyst of the invention is used, the quandricyclane yield exhibits a linear increasing trend with time, and the yield can realize as high as 95% within 8 hours.

By comparing Example 1 with Comparative Examples 1 to 3 in Table 1, it can be seen that under the same circumstances, the quandricyclaine yield achieved by the composite catalyst of the invention is far away higher than that achieve by a single organic photo-sensitizer, a single solid photocatalyst and a simply physical mixture of the organic photo-sensitizer and the solid photocatalyst. The result shows that in views of the composite catalyst prepared by the process of the invention, the process in which the organic photo-sensitizer is loaded to the surface or inner channels of the solid photocatalyst is absolutely not a simple process in which one substance is evenly and physically dispersed on the surface of another substance, but a process in which the two substances take certain interactions to produce greater synergetic effects. With respect to the phenomena, a possible reason may reside in that between the organic photo-sensitizers and the solid photocatalyst there is a transfer of photo-generated charges, and the transfer can promote the separation of charges and increase the efficiency of the use of the photo-generated charges in the isomerisation reaction. However, other reasons are not excluded, and they can be further studies in the future.

The experimental results of Examples 2 to 11 in the invention, as shown in Table 1, also show that the composite catalyst according to the invention, within a lower weight ratio range of the catalyst to norbornadiene of 2% to 8%, can achieve the quandricyclane yield of greater than 90% at a temperature ranging from 10 to 70° C. The result demonstrates that the activity of the composite catalyst according to the invention is very high, and thus the amount of the catalyst can be reduced.

In views of the conditions of the catalytic activity test, the norbornadiene reactant is directly used as the reaction medium, and no solvents are present in the reaction. Even if under such conditions, the activity of the composite catalyst according to the invention is still high, while the activities of individual catalysts in the comparative examples are poor. The result demonstrates that the composite catalyst according to the invention can get rid of dependence on dilution solvents in the reaction, which can have advantages to increase the amount of the reactant treated by the catalyst per unit volume. Furthermore, the composite catalysts according to the invention are in a solid state, and the solid form can benefit the recovery and recycling of the catalyst.

Figure 2:
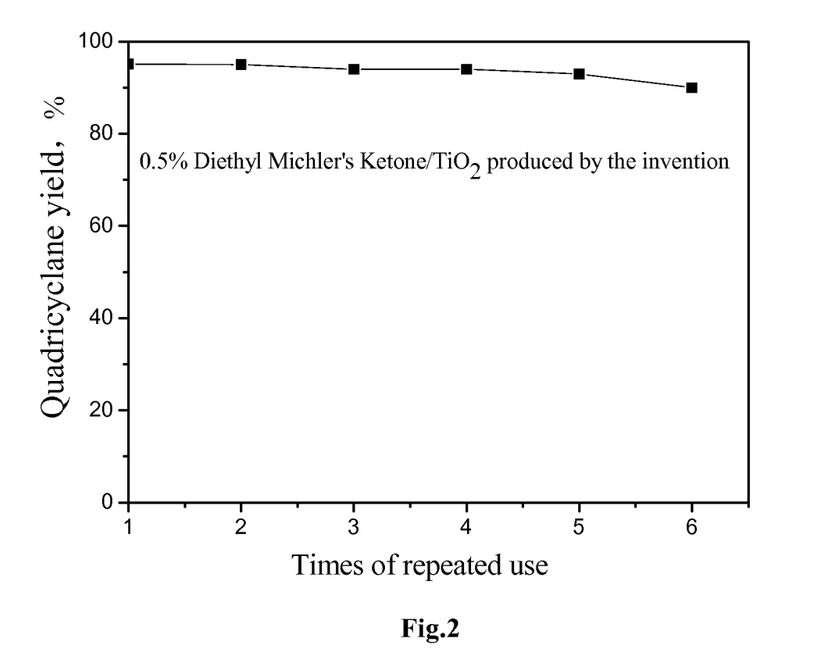
FIG. 2 shows the variation of the quadricyclane yield in the presence of a recycled catalyst according to the invention with time.

As seen in FIG. 2, after the composite catalyst according to the invention is recycled five or six times, a corresponding quandricyclane yield is still high. The result demonstrates that the activity of the composite catalyst according to the invention is stable. Possible reason may reside in that in the process of the invention when the photo-sensitizer is loaded on the solid photocatalyst, the two substances are chemically bound together, so that the organic photo-sensitizer is not easily leached to the reaction medium. Certainly, other reasons which are not known by the inventor and which result in the stability of the catalysts of the invention are not excluded. The stable activity of the catalysts according to the invention is very advantageous to industrial applications thereof.

Figure 3:
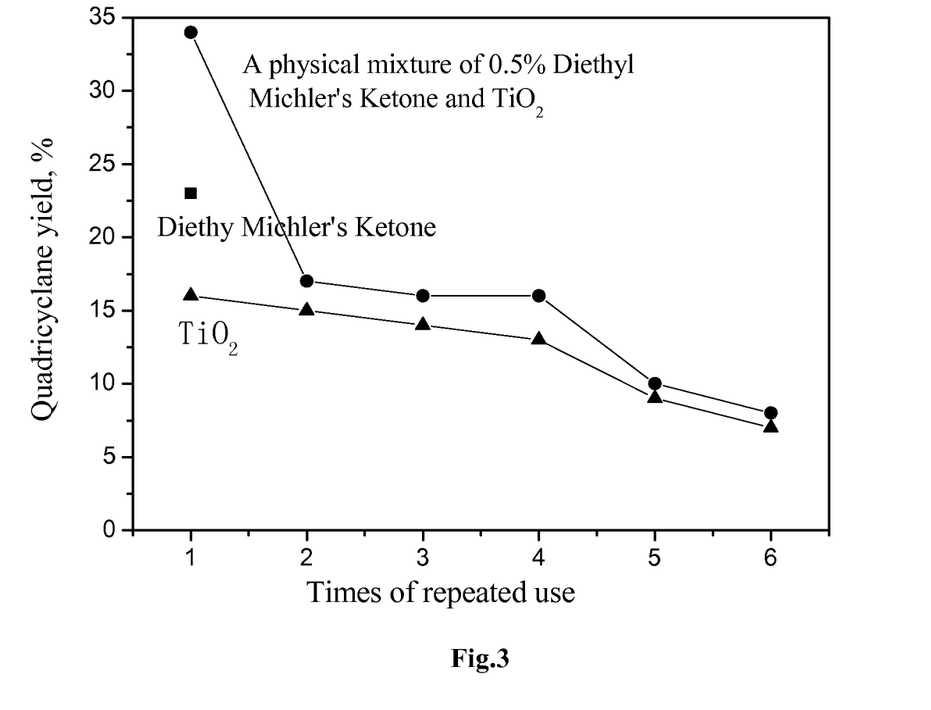
FIG. 3 shows the variation of the quadricyclane yield in the presence of a recycled comparative catalyst with time.

As shown in FIG. 3, because the single organic photo-sensitizer is dissolved in the reaction solution, it cannot be recycled. Although a single solid photocatalyst can be recycled, its activity exhibits a continuously decreased tread. The quadricyclane yield achieved by a simple physical mixture of an organic photo-sensitize and a solid photocatalyst, after the first reaction, will quickly decrease to the level achieved by a single solid photocatalyst, and this result shows that the organic photo-sensitizer therein has leached. The result demonstrates that the activity of the catalysts in the comparative examples will be lost greatly, and thus they are not suitable for repeated application in industry.

Figure 4:
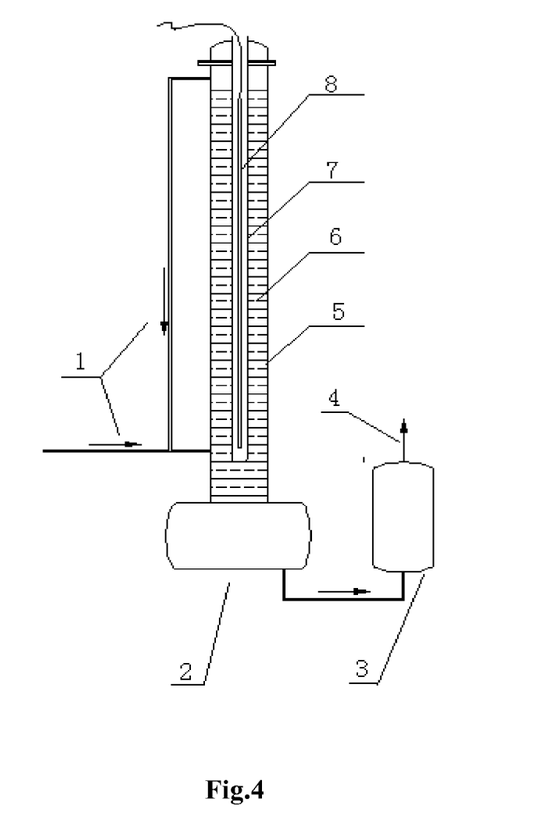
FIG. 4 shows a schematic which represents the process in the first aspect of the invention.

4. Continuous Process for the Production of Highly-pure Quadricyclane According to the Invention: the Reaction-rectification Integral Process The process flow is shown in FIG. 4. The norbornadiene reactant is introduced into a reaction-rectification integral reactor. The reactor comprises a outside stainless steel cylinder having an internal diameter of 6 cm and a height of 110 cm, and a quartz tube having a diameter of 3 cm in the inside. A 6 kW linear high-voltage mercury arc lamp (the lamp length of 103 cm) is arranged in the quartz tube as the ultraviolet light source, and between the quartz and the stainless steel cylinder there is filled with wire gauze structured fillers whose surface is covered with the composite catalyst. The composite catalyst is a diethyl Michler's Ketone loaded on $TiO_2$, wherein the loading amount of the diethyl Michler's Ketone is 0.5% by weight of the $TiO_2$, and the volume ratio of the composite catalyst to the filler is 15%. The norbornadiene reactant is injected into the reactor with the flow rate of 25 ml/min, and the injected norbornadiene flows through the surface and inner channels of the composite catalyst in a form of a very thin liquid film or a gas-liquid mixture, to conduct the isomerisation in the presence of the catalyst and with the ultraviolet light radiation, thereby to produce the reaction product comprising quadricyclane and cokes. The process conditions in the reaction-rectification integral reactor are as follows: the temperature on the top ranges from 90 to 95° C.; the temperature on the bottom ranges from 100 to 105° C.; the pressure is an atmospheric pressure; and the rereflux ratio is 0.8. Under the rectification actions provided by the reaction-rectification integral reactor, unreacted norbornadiene gradually moves toward the top of the reaction-rectification integral reactor and leaves from the top, and after it is condensed via an external condenser, it is re-introduced into the reaction-rectification integral reactor as the recycling reactant. The product quadricyclane and cokes move toward the bottom of the reaction-rectification integral reactor under the rectification actions, and are discharged from the bottom into a distiller to conduct a vacuum distillation. The temperature in the distiller ranges from 60 to 65° C. with the pressure of 90 to 110 mBar. Highly pure quadricyclane is produced on the top of the distiller with a distillation effluent output of 20 ml/min (measured by the gas phase chromatograph, the purity of 99.6%), and on the bottom cokes are produced and discharged. After the 48-hour operation of the whole system, the distillation effluent output and the purity of quadricyclane keep constant, and the result demonstrates that there are no obvious cokes accumulated in the reaction-rectification integral reactor; after 500-hour operation of the whole system, the distillation effluent output of quadricyclane decreases to be 18.7 ml/min, and the purity of the produced quadricyclane slightly decreases to be 99.5%, the purity still meeting the purity requirements. After the system is operated for 500 hours, the ultraviolet light source is extinguished to terminate the reaction. The quartz tube is taken out and observed, and it is found that the tube is still highly transparent, and almost no cokes exist on the surface thereof. The phenomena demonstrates that the process of the invention indeed can continuously and stably produce highly-pure quadricyclane, and the required reaction time is greatly shortened than conventional batch processes.

Figure 5:
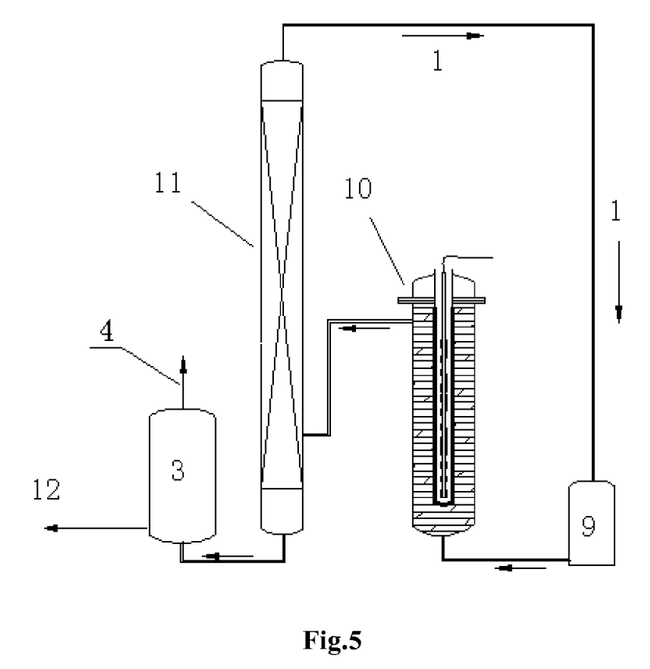
FIG. 5 shows a schematic which represents the process in the second aspect of the invention.

5. Continuous Process for the Production of High-purity Quadricyclane According to the Invention: a Reaction Followed by Rectification Process The height of the reactor is 80 cm; the diameter of the quartz tube is 3 cm; and the internal diameter of the stainless steel reactor is 6cm. A 4 kW linear high-voltage mercury arc lamp (the lamp length of 75 cm) is arranged in the quartz tube as the ultraviolet light source, and the filled catalyst is Ti-SBA-15 loaded with 10 wt % of diethyl Michler's Ketone (shaped into particles having the particle size of 2 to 4 mm). The norbornadiene feedstock is injected to the reactor via a constant-flow pump with the reactant flow rates as shown in Table 2, and the process conditions in the reactor are listed as follows: there are no special requirements to the temperature; the pressure is an atmospheric pressure; and the residence time is shown in the following Table 2. The effluent of the reactor is fed into a rectification column, and the process conditions in the rectification column are as follows: the column height is 110 cm; the column diameter is 6 cm; the temperature on the top of the column ranges from 90 to 95° C.; the temperature on the bottom of the column ranges from 100 to 105° C.; the pressure is an atmospheric pressure; the rereflux ratio is 1. Unreacted norbornadiene is evaporated out on the top of the rectification column, and then it is returned into the feedstock tank to be recycled into the reactor, while quadricyclane and cokes, as the bottoms of the rectification column, are discharged into the distiller and distilled therein at a temperature of 60 to 65° C. and a pressure of 90 to 110 mBar. The evaporation effluent output rate of quadricyclane is shown in the following Table 2. After the 48-hour operation, the evaporation effluent output rate and the purity of the quadricyclane keep constant, and the result demonstrates that no obvious cokes are produced in the reactor.

The resultant quadricyclane is analyzed via the gas phase chromatograph, and the purity are shown in the following Table 2.

TABLE 2

| Number | Reactant flow rate (ml/min) | Reaction residence time (min) | evaporation effluent output rate of quadricyclane (ml/min) | Quadricyclane purity(%) |
|---|---|---|---|---|
| 1 | 8 | 125 | 6 | 99.5 |
| 2 | 10 | 100 | 7.5 | 99.7 |
| 3 | 15 | 67 | 10 | 99.6 |
| 4 | 20 | 50 | 14 | 99.5 |

The invention claimed is:

1. A continuous process for producing highly-pure quadricyclane, comprising the following steps:
   (a) a norbornadiene reactant is introduced into a reaction-rectification integral reactor; the reactor comprises a stainless steel cylinder in the outside, and a quartz tube is arranged inside of the reactor; an ultraviolet light source is arranged in the quartz tube, and rectification fillers and a composite catalyst are filled between the quartz tube and the stainless steel cylinder, wherein the rectification fillers are disorderly mixed with the composite catalyst in the particulate form, or the surface of the rectification fillers is covered with a layer of the composite catalyst; the introduced norbornadiene in a form of a liquid film or a gas-liquid mixture flows through the surface and inner channels of the composite catalyst so that a reaction is conducted to produce a reaction product comprising quadricyclane and cokes; and simultaneously,
   (b) under the rectification action provided by the reaction-rectification integral reactor, the norbornadiene gradually moves toward the top of the reaction-rectification integral reactor and the reaction continues; unreacted norbornadiene leaves from the top and after being condensed, it returns the reaction-rectification integral reactor as the circulating reactant; the product quadricyclane and cokes can move toward the bottom of the reaction-rectification integral reactor under the action of rectification and are discharged from the bottom to a distiller in which the distillation is conducted; at last, the quadricyclane in the purity of more than 99.5% is produced on the top of the distiller, and the cokes are remained in the bottom of the distiller.

2. The process according to claim 1, wherein said composite catalyst comprises:
   a solid photocatalyst, which is selected from $TiO_2$, Ti-MCM-41, Ti-SBA-15, ZnO, $WO_3$, $Ta_2O_5$ or $SrTiO_3$; and
   an organic photo-sensitizer loaded on the surface or channels of the solid photocatalysts, the organic photo-sensitizer is selected from benzophenone, acetophenone, Michler's Ketone, tetraethyl Michler's Ketone or diethyl Michler's Ketone;
   wherein the organic photo-sensitizer is present in an amount of 0.5 to 20% by weight of the solid photocatalyst.

3. The process according to claim 1, wherein the process conditions in the reaction-rectification integral reactor are as follows: temperature on the top of the reactor ranges from 90 to 95° C.; temperature on the bottom of the reactor ranges from 100 to 105° C.; pressure is an atmospheric pressure; and reflux ratio ranges from 0.5 to 2.

4. The process according to claim 1, wherein the process conditions in the distiller are as follows: temperature ranges from 60 to 65° C., and pressure ranges from 90 to 110 mBar, being gauge pressures.

5. A continuous process for producing highly-pure quadricyclane, comprising the following steps:
   (a) a norbornadiene reactant is introduced into a reactor; the reactor comprises a stainless steel cylinder in the outside, and a quartz tube is arranged inside of the reactor; an ultraviolet light source is arranged in the quartz tube, and a composite catalyst is filled between the quartz tube and the stainless steel cylinder; the introduced norbornadiene flows through the surface and inner channels of the composite catalyst in a form of a liquid film so that a reaction is conducted to produce a reaction product comprising quadricyclane and cokes; and then
   (b) all the materials are fed into a rectification column, and under the rectification action, unreacted norbornadiene, as the tops, leaves from the top of the rectification column and returns to the aforesaid reactor as the circulating reactant; the quadricyclane and cokes, as the bottoms, leave the rectification column; and then
   (c) the aforesaid bottoms are fed into a distiller to conduct distillation; the quadricyclane in the purity of more than 99.5% is produced on the top of the distiller, and cokes are remained in the bottom of the distiller; wherein said composite catalyst comprises:
   a solid photocatalyst, which is selected from $TiO_2$, Ti-MCM-41, Ti-SBA-15, ZnO, $WO_3$, $Ta_2O_5$ or $SrTiO_3$; and
   an organic photo-sensitizer loaded on the surface or channels of the solid photocatalyst, the organic photo-sensitizer is selected from benzophenone, acetophenone, Michler's Ketone, tetraethyl Michler's Ketone or diethyl Michler's Ketone;
   wherein the organic photo-sensitizer is present in an amount of 0.5 to 20% by weight of the solid photocatalyst.

6. The process according to claim 5, wherein the process conditions in the reactor are as follows: there are no specific requirements to the temperature, and the pressure is an atmospheric pressure.

7. The process according to claim 5, wherein the process conditions in the rectification column are as follows: the height of the column is not lower than 100 cm; the temperature on the top of the column is from 90 to 95° C.; the temperature on the bottom of the column is from 100 to 105° C.; the pressure is an atmospheric pressure, and the reflux ratio ranges from 0.5 to 2.

8. The process according to claim 5, wherein the process conditions in the distiller are as follows: the temperature ranges from 60 to 65° C., and the pressure ranges from 90 to 110 mBar, being gauge pressure.

\* \* \* \* \*